| United States Patent [19] | [11] Patent Number: 4,755,612 |
|---|---|
| Vacca et al. | [45] Date of Patent: Jul. 5, 1988 |

[54] INTERMEDIATE COMPOUNDS RESULTING FROM METHOD FOR FORMING A DIHYDROGEN-PHOSPHATE INOSITOL

[75] Inventors: Joseph P. Vacca, Telford; S. Jane deSolms, Norristown, both of Pa.

[73] Assignee: Merck & Co., Inc., Rahway, N.J.

[21] Appl. No.: 75,164

[22] Filed: Jul. 20, 1987

[51] Int. Cl.$^4$ .......................................... C07D 317/46
[52] U.S. Cl. ................................................. 549/220
[58] Field of Search ........................................ 549/220

[56] References Cited

PUBLICATIONS

Krylova et al., Chem. Abs. 93, 95518g, (1980).
Krylova et al., "Investigations in the Field of Derivatives of Asymmetrically Substituted Myo-Inositol", *Zh. Org. Khim.*, 16, No. 2, pp. 315–322, Feb. 1980.
Mancuso et al., "Oxidation of Long-Chain and Related Alcohols to Carbonyls by Dimethyl Sulfoxide 'Activated' by Oxalyl Chloride", *J. Org. Chem.*, 43, No. 12, pp. 2480–2482 (1978).
House, H. O. *Modern Synthetic Reactions*, 2nd ed., pp. 45–54 (1972).
Fieser et al., *Reagents for Organic Chemistry*, vol. 1, pp. 1049–1055 (1977).
Ozaki et al., "Total Synthesis of Optically Active Myo-Inositol 1,4,5-Tris(Phosphate)", *Tet. Let.*, 27, No. 27, pp. 3157–3160 (1986).

*Primary Examiner*—Nicky Chan
*Assistant Examiner*—Wendy B. Davis
*Attorney, Agent, or Firm*—Raymond M. Speer; Hesna J. Pfeiffer

[57] ABSTRACT

This invention relates to novel intermediate compounds resulting from a method for forming a dihydrogen-phosphate inositol from a protected or unprotected inositol that comprises at least two vicinal trans hydroxy groups that are unprotected. This method results in each of the unprotected hydroxy groups of the inositol, which can contain from two to six unprotected hydroxy groups, being converted to a dihydrogen-phosphate group and each protected group being converted to a free hydroxy group. The method permits one to make such compounds in very few steps and in very high yields.

4 Claims, No Drawings

INTERMEDIATE COMPOUNDS RESULTING FROM METHOD FOR FORMING A DIHYDROGEN-PHOSPHATE INOSITOL

BACKGROUND OF THE INVENTION

This invention relates to novel intermediate compounds resulting from a method for forming a dihydrogen-phosphate inositol from a protected or unprotected inositol that comprises at least two vicinal trans hydroxy groups that are unprotected. This method results in each of the unprotected hydroxy groups of the inositol, which can contain from two to six unprotected hydroxy groups, being converted to a dihydrogen-phosphate group and each protected group being converted to a free hydroxy group. The method permits one to make such compounds in very few steps and in very high yields.

Specifically, the method is useful for making myo-inositol 1,4,5-trisphosphate, myo-inositol 1,3,4-trisphosphate, myo-inositol 2,4,5-trisphosphate, myo-inositol 1,3,4,5 tetrakisophosphate and deuterium and tritium labelled derivatives thereof. Such compounds, which exist in nature, have been referred to as "second messengers".

One of the control mechanisms for regulation of intracellular $Ca^{2+}$ ion concentration involves activation of membrane receptors followed by signal transduction and the release of a modulatory substance. Recent studies provide compelling evidence that activation of these $Ca^{+2}$ mobilizing receptors results in hydrolysis of phosphatidyl-inositol-4,5-biphosphate, giving rise to D-myo-inositol-1,4,5-trisphosphate ($IP_3$). $IP_3$ directly mediates release of calcium from intracellular stores. For an excellent review of second messengers and their function see Berridge, "The Molecular Basis of Communication within the Cell", *Scientific American*, October, 1985 and Berridge et al., "Inositol Trisphosphate, a Novel Second Messenger in Cellular Signal Transduction", *Nature*, Vol. 312, Nov. 22, 1984.

It is desirable to utilize the second messengers in order to analyse their biochemical pathways within the cell and to analyse the effects of the second messengers on cells. Also, it would be desirable to label the second messengers, which would assist one in establishing a competitive binding assay to determine whether or not other compounds are capable of binding to the second messenger receptors. However, very small quantities of the second messengers are produced naturally. Thus, it would be highly desirable to produce them synthetically.

Numerous attempts have been made to synthesize the inositol second messengers. However, all of the methods have resulted in the final product being produced in very low yields. Such low yields are primarily caused by the difficulty of adding a dihydrogen phosphate group to the vicinal trans hydroxy group(s) of inositol. For example, see S. J. Angyal et al, "Polyphosphorylation of Polyols, the Synthesis of Myo-Inositol Pentaphosphates," *Aust. J. Chem.*, 1968, 21, pp. 391–404; V. N. Krylova et al., "Investigations in the Field of Derivatives of Asymmetrically Substituted Myo-inositol", *Zhurnal Organicheskoi Khimii*, Vol. 16., No. 2, pp. 315–322, February, 1980; and Ozaki et al., "Total Synthesis of Optically Active Myo-Inositol 1,4,5 Tris(phosphate)", *Tetrahedron Letters*, Vol. 27, No. 27, pp. 3157–3160, 1986.

SUMMARY OF THE INVENTION

The present invention relates to novel intermediate compounds resulting from a method for forming a dihydrogen-phosphate inositol from a protected or unprotected inositol that comprises at least two vicinal trans hydroxy groups. More precisely, the method is a method for forming a compound having the general structure I:

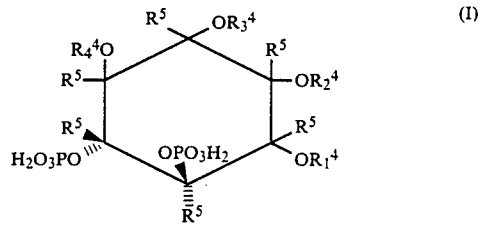

which comprises:

(A) contacting an inositol having the general structure II:

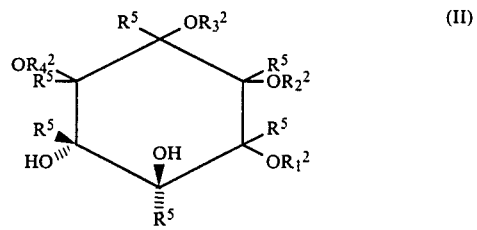

with a compound having the general structure III:

in an aprotic medium comprising a strong base to form a compound having the general structure IV:

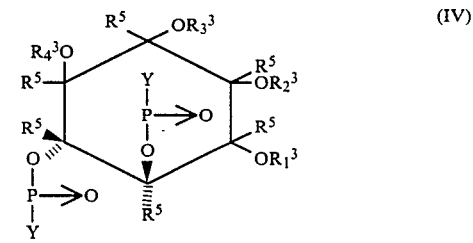

(B) converting the compound having the general structure IV to the compound having the general structure I and (C) isolating the compound having the general structure I, wherein:

L is a suitable leaving group;

Y is selected from the group consisting of: $(Z^1-O)_2$ and

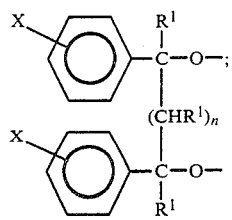

each $Z^1$ is independently selected from the group consisting of:

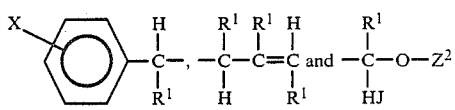

each $Z^2$ is independently selected from the group consisting of:
$C_{1-4}$ alkyl and

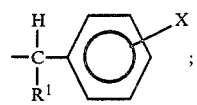

each $R^1$ is independently selected from the group consisting of: H, $C_{1-4}$ alkyl and

each X is independently selected from the group consisting of: H, halogen, $C_{1-4}$ alkyl, $C_{1-4}$ alkoxy, $C_{1-4}$ alkylthio, carboxyl, carboxyl $C_{1-4}$ alkyl, nitro, —$CF_3$ and hydroxy;

$R_1^2$, $R_2^2$, $R_3^2$ and $R_4^2$ is each independently selected from the group consisting of:
H, $Z^1$, two vicinal $R^2$ groups are one

to form a five-membered ring and

each $Z^3$ is independently selected from the group consisting of: H, $C_{1-4}$ alkyl,

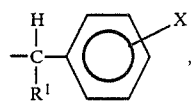

and each $Z^3$ is an alkyl joined to form a 5 or 6 membered cycloalkyl group;

$R_1^3$, $R_2^3$, $R_3^3$ and $R_4^3$ is each independently selected from the group consisting of:
$Z^1$, two vicinal $R^3$ groups are one

to form a five membered ring and

$R_1^4$, $R_2^4$, $R_3^4$ and $R_4^4$ is each independently selected from the group consisting of: —H and —$PO_3H_2$;
n is 0-3;
each $R^5$ is independently selected from the group consisting of H, $^3H$ and $^2H$;
wherein:
(i) $R_1^2=R_1^3$; $R_2^2=R_2^3$; $R_3^2=R_3^3$; $R_4^2=R_4^3$ with the proviso that when any $R^2$ is H, then the corresponding $R^3$ is

and
(ii) any $R^4$ is —$PO_3H_2$ only when the corresponding $R^3$ is

The intermediate compounds of the invention have the general structure IV, defined hereinabove.

DETAILED DESCRIPTION OF THE INVENTION

The present invention relates to novel intermediate compounds resulting from a method for forming a dihydrogen-phosphate inositol from a protected or unprotected inositol that comprises at least two vicinal trans hydroxy groups. The method is only three steps and produces high yields of the desired dihydrogen-phosphate inositol. Also, the method can be utilized to label, with deuterium or tritium, the dihydrogen-phosphate inositol. The method is particularly useful for synthesizing the four naturally occurring dihydrogen-phosphate inositols.

The starting material for the method is a protected or unprotected inositol that comprises at least two vicinal trans hydroxy groups. Inositol is a hexahydroxycyclohexane. What is meant in the present invention by "protected" inositol is that at least one hydroxy group is chemically modified so that it remains inert during the phosphorylation step. Also, what is meant by "unprotected" is that the six hydroxy groups of the inositol are free hydroxy groups. The method of the invention converts each of the hydroxy grups to a dihydrogen-phosphate group.

It is believed that any protecting group can be utilized so long as it remains inert during the phosphorylation step. However, the preferred protecting groups are such that the starting material of the invention is a compound of the general formula II:

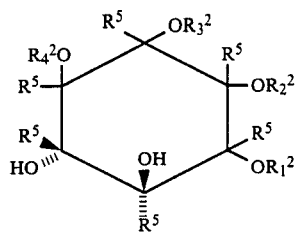

wherein: $R_1^2$, $R_2^2$, $R_3^2$ and $R_4^2$ is each independently selected from the group consisting of:
H, $Z^1$, two vicinal $R^2$ groups are one

to form a five-membered ring, which is

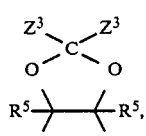

and

Y is selected from the group consisting of:
$(Z^1-O)-_2$ and

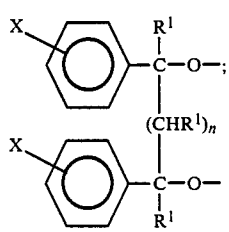

each $Z^1$ is independently selected from the group consisting of:

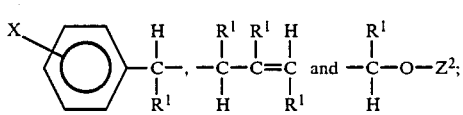

each $Z^2$ is independently selected of $C_{1-4}$ alkyl and

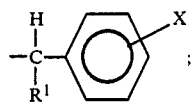

each $Z^3$ is independently selected from the group consisting of:
H, $C_{1-4}$ alkyl,

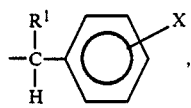

and two vicinal $Z^3$ groups are an alkyl joined to form a 5 or 6 membered cycloalkyl group, i.e.

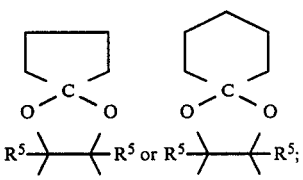

each $R^1$ is independently selected from the group consisting of: —H, —$C_{1-4}$ alkyl and

each X is independently selected from the group consisting of H, halogen, $C_{1-4}$ alkyl, $C_{1-4}$ alkoxy, $C_{1-4}$ alkylthio, carboxyl, carboxyl $C_{1-4}$ alkyl, nitro, —$CF_3$ and hydroxy;
each $R^5$ is independently selected from the group consisting of H, $^2$H and $^3$H;
and n is from 0 to 3.
Each of the compounds of the general structure II can be prepared readily by one of ordinary skill in the art.
Preferred starting materials are selected from the group consisting of:

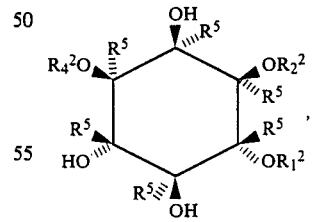

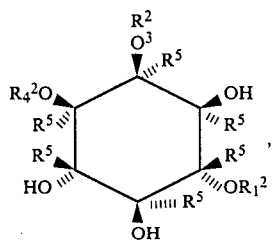

-continued

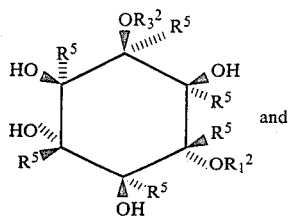

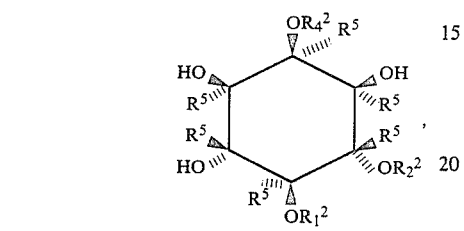

wherein $R_1^2$, $R_2^2$, $R_3^2$, $R_4^2$ and $R^5$ are as defined hereinabove. Such compounds are preferred because they are useful to make the naturally occurring dihydrogenphosphate inositols. Even more preferred starting materials are:

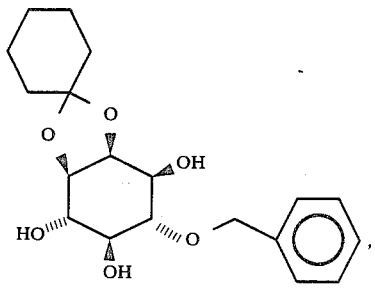

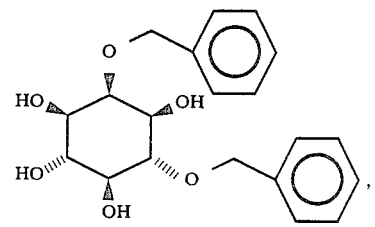

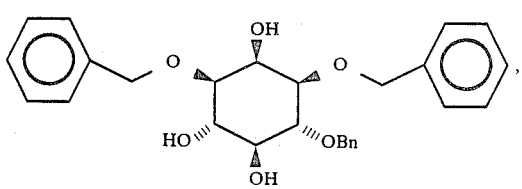

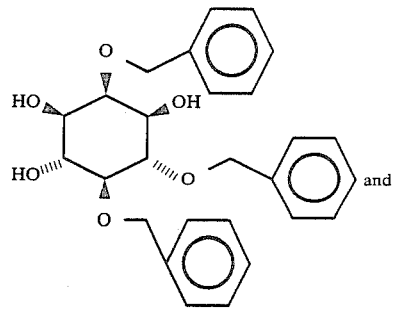

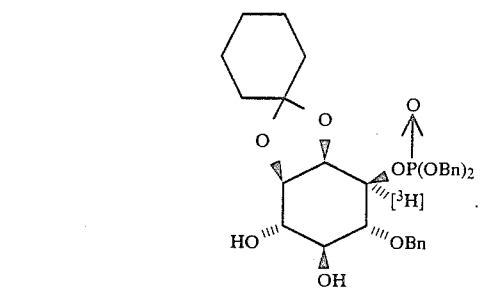

These compounds contain the preferred protecting groups. (It should be noted that Bn represents a benzyl group).

The first step of the method is the phosphorylation step. This step entails contacting the starting material with a phosphorylating agent of the invention in a suitable aprotic medium comprising a strong base. It is the use of the phosphorylating agent of the invention under strong basic conditions that results in the high yield of the reaction product.

The phosphorylating agents of the invention have the general structure III:

$$Y-\overset{\overset{O}{\uparrow}}{P}-L \quad (III)$$

wherein L is a suitable leaving group and Y is selected from the group consisting of: $(Z^1-O-)_2$ and

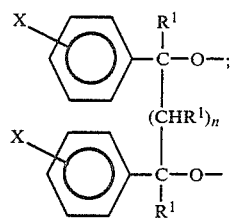

wherein X, $R^1$, n and $Z^1$ are as defined hereinabove.

It is believed that L can be any suitable leaving group that can be displaced during the phosphorylation step, which is a standard $S_N2$ displacement reaction. Nonlimiting examples of suitable leaving groups are: —Cl, —Br, —OSO₂CF₃,

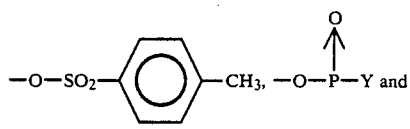, 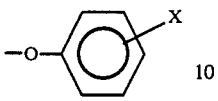

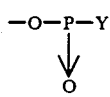

wherein Y is as defined hereinabove, with

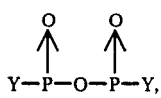

being preferred, thus the preferred phosphorylating agent has the general structure:

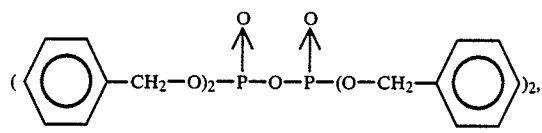

with each Y group being the same or different, but preferably the same. Even more preferred is when X and $R^1$ of each Y group are H and n is O. Yet more preferred phosphorylating agents are:

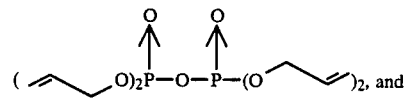

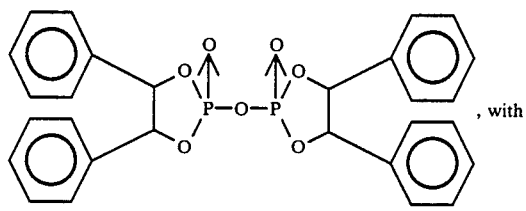, with

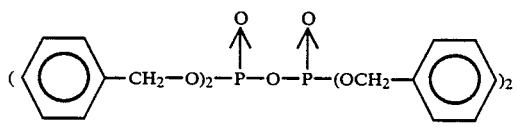

being the most preferred.

Each of the compounds of general structure III can be prepared readily by one of ordinary skill in the art.

The phosphorylating step should be carried out in an aprotic medium. Nonlimiting examples of suitable aprotic mediums are tetrahydrofuran, dimethyl formamide, 1,2 dimethoxyethane and dimethyl sulfoxide, with tetrahydrofuran and dimethyl formamide being preferred.

It is essential that the aprotic medium comprise a strong base. A strong base is any compound that can deprotonate an alcohol in an aprotic medium. Nonlimiting examples of suitable strong bases are KH, NaH, KO—C—(CH$_3$)$_3$, n-butyl Li and lithium diisopropylamide, with KH and NaH being preferred.

The phosphorylation step results in the formation of the intermediate compounds of the invention, which have general structure IV:

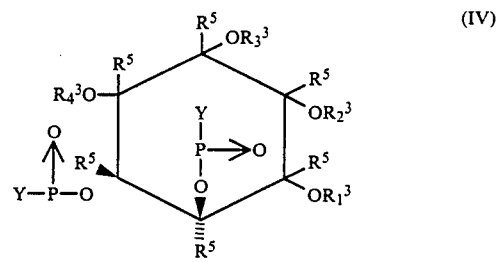 (IV)

wherein:

$R_1^3$, $R_2^3$, $R_3^3$ and $R_4^3$ is each independently selected from the group consisting of $Z^1$, two vicinal $R^3$ groups are one

to form a five membered ring and

wherein $Z^1$, $Z^3$ and Y are as defined hereinabove and $R^5$ is as defined hereinabove, However, it is essential to note that the choice of each $R^3$ is dependent upon the choice of the corresponding $R^2$. Thus, $R_1^2=R_1^3$, $R_2^2=R_2^3$, $R_3^2=R_3^3$ and $R_4^2=R_4^3$, with the proviso that when any $R^2$ is H, then the corresponding $R^3$ is

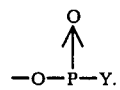

Similarly, the preferred intermediate compounds of general structure IV are the intermediate compounds corresponding to the preferred starting materials of general structure II and preferred phosphorylating agent of general structure III. All of the intermediate compounds of the invention are novel.

It is preferred that the intermediate compound be isolated from the aprotic medium. This can be carried out by standard techniques, e.g. silica gel chromatography. Isolation of the intermediate compound makes for a much easier isolation of the final product, i.e. the dihydrogen-phosphate inositol.

The second step of the method of the invention consists of converting the intermediate compound having the general structure IV to a compound having the general structure I:

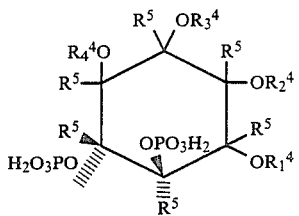

wherein: $R_1^4$, $R_2^4$, $R_3^4$ and $R_4^4$ is each independently selected from the group consisting of —H and —PO$_3$H$_2$ and $R^5$ is as defined hereinabove.

The conversion step converts each $R^3$ that is

to —PO$_3$H$_2$ and the other $R^3$ groups to H. The compound having the general structure I is the final product, the dihydrogen-phosphate inositol.

The conversion step can be carried out by any means so long as the dihydrogen-phosphate inositol is formed. An easy method of conversion is to subject the intermediate compound to hydrogenolysis with H$_2$ in the presence of Pd/C in alcohol, e.g. ethanol. Hydrogenolysis removes all of the benzyl groups, if any, to form the appropriate group at each of the positions that contained a benzyl group. The positions of the intermediate compound that do not have a benzyl can be converted to the appropriate final product by treatment with a mild acid, e.g. acetic acid. This conversion method can be carried out with the intermediate compound of the general structure IV in the aprotic medium or isolated from the aprotic medium. If the intermediate compound of general structure IV contains any 2-alkenyl groups, then it is desirable to remove them first before removing any benzyl groups which may exist. A 2-alkenyl group can be removed by heating the intermediate compound with a catalytic amount of Pd/C and tosic acid in methanol (see, for example, R. Scheffold et al., *Angew Chem.* [Eng] 1976, 15, 558.)

The preferred compounds of the general structure I are the compounds produced from the preferred compounds of the general structure III.

The compound of the general structure I now can be isolated by standard techniques.

It should be noted that the present invention permits one to label, with $^3$H or $^2$H, the one position of myo-inositol-1,4,5 triphosphate. This can be carried out by utilizing as the starting material:

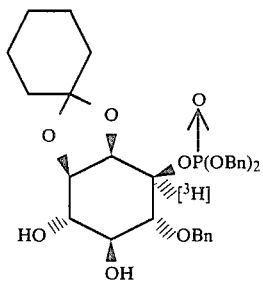

The method of the invention results in such starting material being converted to 1-[$^3$H]-myo-inositol 1,4,5-trisphosphate.

It should be noted that although all of the inositol compounds illustrated hereinabove depict only one enantiomer; the invention includes the other enantiomer as well.

EXAMPLE I

Preparation of Myo-1,4,5-inositol-trisphosphate

Phosphorylation of 4-O-Benzyl-1:2-O-cyclohexylidene-myoinositol; 6-O-Benzyl-2:3-O-cyclohexylidene-myo-inositol 1,4,5-hexabenzyl-trisphosphate 4-O-Benzyl-1:2-O-cyclohexylidene-myo-inositol (0.197 g, 0.56 mmol) was dissolved in 25 ml of DMF and tetrabenzylpyrophosphate (1.51 g, 2.8 mmol) was added. The reaction was cooled to 0° C. and sodium hydride (0.27 g, 50% in oil) was added. After 30 min a ppt was noticed. After 1 hour the reaction was complete (tlc, 60% EtOAc/Hexane) and was worked up by concentrating under high-vaccum. The residue was triturated in CH$_2$Cl$_2$, filtered, concentrated and chromatographed (SiO$_2$, 60% EtOAc/Hexane) to give the product as an oil. (80%[α]$_D$=−4.5°, CHCl$_3$).

Myo-inositol-1,4,5-trisphosphate

6-O-Benzyl-2:3-O-cyclohexylidene-myo-inositol-1,4,5-hexabenzyl-trisphosphate (0.49 g, 0.434 mmol) was dissolved in 50 ml of 90% EtOH and 0.5 g of 10% Pd/C was added. This was shaken on a mini-Parr apparatus under an atmosphere of H$_2$ (50 psig) for 3 hours, filtered and 3 ml of acetic acid was added. After stirring for 18 hours the reaction was concentrated to dryness, the residue triturated with CH$_2$Cl$_2$, and the remaining residue dissolved in a minimum amount of water. Any ppt present was filtered and about 6–7 eq of 10% NaOH solution was added. The solution was then diluted with MeOH to precipitate the product as a hexa-sodium salt which was dried at 40° C. to give the product as a trihydrate. [α]$_D$=−30°, (H$_2$O, C=1 mg/ml, pH=10 (cyclohexylamine added to insure basicity)).

EXAMPLE II

Preparation of Myo-inositol 1,3,4-Trisphosphate 2,5,6-Tri-O-benzyl-myo-inositol-1,3,4-hexabenzyltrisphosphate To a solution of 2,4,5-Tri-O-benzyl-myo-inositol (0.160 g, 0.36 mmol) and tetrabenzylpyrophosphate (1.15 g, 2.1 mmol) in 25 ml of DMF (0° C.) was added sodium hydride (0.102 gm, 2.1 mmol, 50% in oil). The reaction was stirred at 0° C. for 3 hours and worked up by concentrating to dryness. The residue was triturated with CH$_2$Cl$_2$, filtered, concentrated and chromatographed (EtOAc/Hexane, 1:1, SiO$_2$) to give the product (330 mg, 75%) as an oil.

Myo-inositol-1,3,4-trisphosphate 2,5,6-Tri-O-benzyl-myo-inositol-1,3,4-hexabenzyl-trisphosphate (0.22 mg, 0.18 mmol) was dissolved in 15 ml of 95% EtOH in a mini-Parr apparatus and 220 mg of 10% Pd/C was added. This was skaken under a hydrogen atmosphere for 3 hours and the catalyst was filtered off. The filtrate was concentrated and worked up, as in EXAMPLE I, to give the product as a penta-sodium salt (64%).

EXAMPLE III

Preparation Myo-inositol 2,4,5-trisphosphate

1,3,4-Tri-O-benzyl-myo-inositol 2,4,5-hexabenzyltrisphosphate

To a solution of 1,3,4-Tri-O-benzyl-myo-inositol (0.160 g, 0.36 mmol) and tetrabenzylpyrophosphate (1.15 g, 2.1 mmol) in 25 ml of DMF (0° C.) was added sodium hydride (0.102 gm, 2.1 mmol, 50% in oil). The reaction was stirred at 0° C. for 3 hours and worked up by concentrating to dryness. The residue was triturated with CH$_2$Cl$_2$, filtered, concentrated and chromatographed (EtOAc/Hexane, 1:1, SiO$_2$) to give the product (283 mg, 64%) as an oil.

Myo-inositol-2,4,5 trisphosphate 1,3,4-Tri-O-Benzyl-myo-inositol-2,4,5-hexabenzyl-trisphosphate (0.19 mg, 0.15 mmol) was dissolved in 15 ml of 95% EtOH in a mini-Parr apparatus and 190 mg of 10% Pd/C was added. This was shaken under a hydrogen atmosphere for 3 hours and the catalyst was filtered off. The filtrate was concentrated and worked up, as in EXAMPLE I, to give the product as its hexa-sodium salt.

EXAMPLE IV

Preparation of Myo-inositol 1,3,4,5-tetrakisophosphate

2,6-Di-O-Benzyl-myo-inositol 1,3,4,5-octabenzyl-tetrakisphosphate

To a solution of 2,4-Di-O-benzyl-myo-inositol (0.360 g, 1.0 mmol) and tetrabenzylpyrophosphate (3.22 g, 6.0 mmol) in 45 ml of DMF (0° C.) was added sodium hydride (0.288 g, 6.0 mmol, 50% in oil). The reaction was stirred at 0° C. for 3 hours and then warmed to 25° C. for another 3 hours. The reaction was worked up by concentrating to dryness and the residue was triturated with CH$_2$Cl$_2$, filtered, concentrated and chromatographed (EtOAc/Hexane, 1:1, SiO$_2$) to give the product (820 mg, 59%) as an oil.

Myo-inositol 1,3,4,5 tetrakisphosphate 2,6-Di-O-benzyl-myo-inositol 1,3,4,5-octabenzyl-tetrakisphosphate (0.810 g, 0.58 mmol) was dissolved in 45 ml of 95% EtOH in a mini-Parr apparatus and 0.900 g of 10% Pd/C was added. This was shaken under a hydrogen atmosphere for 3 hours and the catalyst was filtered off. The filtrate was concentrated and worked up, as in Example I, to give the product as its tetra-sodium salt.

EXAMPLE V

Preparation of 1-[$^3$H]-myo-inositol 1,4,5-Trisphosphate

1-[$^3$H]-4-O-benzyl-2:3-O-cyclohexylidene-myo-inositol 1,4,5-hexabenzyl-trisphosphate To a solution of 1-[$^3$H]-4-O-benzyl-2:3-O-cyclohexylidene-myo-inositol 1-dibenzylphosphate (0.010 g, 0.016 mmol) and tetrabenzylpyrophosphate (0.026 g, 0.048 mmol) in 2 ml of DMF (0° C.) was added sodium hydride (0.002 gm, 0.043 mmol, 50% in oil). The reaction was stirred at 0° C. for 3 hours and worked up by concentrating to dryness. The crude reaction was chromatographed (SiO$_2$ prep. plate, EtOAc/Hexane, 1:1) to give 10.6 mg, (60%) of product.

1-[$^3$H]-Myo-inositol-1,4,5-trisphosphate

1-[$^3$H]-4-O-Benzyl-2:3-O-cyclohexylidene-myo-inositol-1,4,5-hexabenzyl-trisphosphate (0.010 g, 0.008 mmol) was dissolved in 2 ml of 90% EtOH and 0.01 g of 10% Pd/C was added. Hydrogen gas was bubbled through the flask for 10 minutes and then the flask was stoppered tightly and stirred for 18 hours after which time 3 mls of acetic acid was added. After an additional 20 hours, the reaction was filtered and concentrated and the residue triturated with CH$_2$Cl$_2$ to give the product as a glassy solid.

What is claimed is:

1. A compound having the general structure IV:

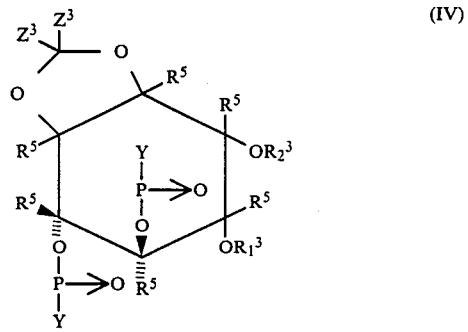

wherein

Y is (Z$^1$—O)$_2$;

each Z$^1$ is independently selected from the group consisting of:

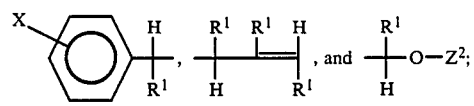

each Z$^2$ is independently selected from the group consisting of C$_{1-4}$ alkyl and

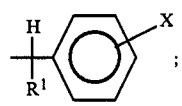

each R$^1$ is independently selected from the group consisting of H, C$_{1-4}$ alkyl and

each X is independently selected from the group consisting of H, halogen, C$_{1-4}$ alkyl, C$_{1-4}$ alkoxy, C$_{1-4}$ alkylthio, carboxyl, carboxyl C$_{1-4}$ alkyl, nitro, —CF$_3$, and hydroxy;

R$_1{}^3$ and R$_2{}^3$ are each independently selected from the group consisting of Z$^1$ and

each Z$^3$ is independently selected from the group consisting of H, C$_{1-4}$ alkyl, and

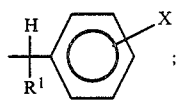
or each $Z^3$ is an alkyl joined to form a 5 or 6 membered cycloalkyl group; and
each $R^5$ is independently selected from the group consisting of H, $^3$H, and $^2$H.
2. A compound in accordance with claim 1 having the general structure:
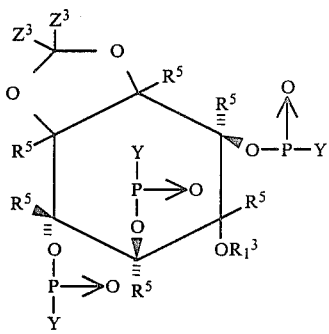
3. A compound in accordance with claim 2 selected from the group consisting of:
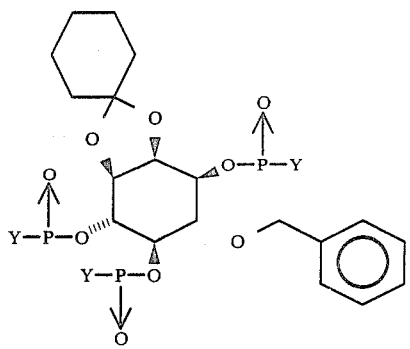
and
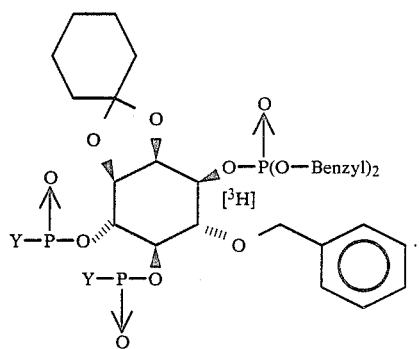
4. A compound in accordance with claim 3 wherein Y is
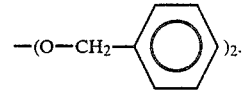
* * * * *